United States Patent [19]
Kneuper et al.

[11] Patent Number: 5,919,987
[45] Date of Patent: *Jul. 6, 1999

[54] PREPARATION OF ALCOHOLS AND/OR ALDEHYDES

[75] Inventors: Heinz-Josef Kneuper, Mannheim; Maik Aron, Weisenheim; Frank-Michael Korgitzsch, Bad Dürkheim; Michael Nilles, Ludwigshafen; Wolfgang Harder, Weinheim; Michael Röper, Wachenheim; Rocco Paciello, Bad Dürkheim, all of Germany

[73] Assignee: BASF Aktiengesellschaft, Ludwigshafen, Germany

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/716,216

[22] PCT Filed: Mar. 6, 1995

[86] PCT No.: PCT/EP95/00825

§ 371 Date: Sep. 13, 1996

§ 102(e) Date: Sep. 13, 1996

[87] PCT Pub. No.: WO95/25080

PCT Pub. Date: Sep. 21, 1995

[30] Foreign Application Priority Data

Mar. 16, 1994 [DE] Germany .................. 44 08 950

[51] Int. Cl.⁶ .................................................. C07C 45/00
[52] U.S. Cl. .................................... 568/451; 568/444
[58] Field of Search ................................. 568/444, 451

[56] References Cited

U.S. PATENT DOCUMENTS

| | | | |
|---|---|---|---|
| 2,880,241 | 3/1959 | Hughes et al. | 260/604 |
| 3,984,478 | 10/1976 | Homeier | 260/604 |
| 4,148,830 | 4/1979 | Pruett et al. | 260/604 |
| 4,329,521 | 5/1982 | Homeier et al. | 568/909 |
| 4,400,547 | 8/1983 | Dawes et al. | 568/454 |
| 4,740,626 | 4/1988 | Bahrmann et al. | 568/454 |
| 5,041,685 | 8/1991 | Alvila et al. | 568/455 |
| 5,387,719 | 2/1995 | Kneuper et al. | 568/455 |

FOREIGN PATENT DOCUMENTS

| | | |
|---|---|---|
| A 504814 | 9/1992 | European Pat. Off. . |
| 2604545 | 8/1977 | Germany . |
| 3338340 | 5/1984 | Germany . |
| WO 82/03856 | 11/1982 | WIPO ............. 568/451 |

OTHER PUBLICATIONS

J. Falbe. "New Synthesis with Carbon Monoxide", Reactivity and Structure Concepts in Organic Chemistry, vol. 11, 1980, Springer–Verlag, Berlin, pp. 38–73 and 95–100.

Heil et al, "Einfluss . . . " (translated . . . ) "Influence of the olefin structure on the speed of reaction", Chem. Ber. 102, pp. 2238–2240 (1969).

Bernhard Fell et al, "Zur Frage . . . " ( . . . translated) "Concerning the formation of isomers in the hydroformulation of higher molecular olefins . . . ", Tetrahedron Letters No. 29, pp. 3261–3266 (1968), Pergammon Press.

Ludwig, "Industrial hydrogenation of aldehydes", Hydrocarbon Processing/Mar. 1993, pp. 67–74.

G. P. Schanzenbach, "Sensors for machinery monitoring", Hydrocarbon Processing/Feb. 1975, pp. 85–88.

Von K. Bott, "Aldehydes and Successive Products from the Ox0–Synthesis of Double Bond Isomerized N–Olefins" Fette Seifen/Anstrichmittel 72 (1974), pp. 443–446.

Mitsuo Yamaguchi, Journal of the Chemical Society of Japan (Kogyo Kagaku Zasshi), vol. 72 (1969), pp. 671–675 (no translation available).

Ullmann's Encyc. of Ind. Chem. vol. A5, 5th Ed. (1986), pp. 239 "4.1.1. Aldehyde Oxidation".

Ullmann's Encyc. of Ind. Chem., vol. A1, 5th Ed. (1986), pp. 279 et seq. (Alcohols, Aliphatic).

Ullmann's Encyc. of Ind. Chem., vol. A2, 5th Ed. (1986), p. 1 et seq. (Amines, Aliphatic).

*Primary Examiner*—José G. Dees
*Assistant Examiner*—Barbara Badio
*Attorney, Agent, or Firm*—John H. Shurtleff

[57] ABSTRACT

An industrial preparation of aldehydes and/or alcohols from olefins of more than 3 carbon atoms by a catalytic hydroformylation of the olefin reactant at a pressure of from 50 to 1000 bar and a temperature of from 50 to 180° C. in the presence of an uncomplexed rhodium catalyst homogeneously dissolved in the reaction medium. The catalytic activity of the rhodium is maintained, first by extracting it from the initially discharged reaction mixture by means of an aqueous solution of a nitrogen-containing complexing agent such as sulfonated or carboxylated pyridines, quinolines or the like. In a recycle of the complexed rhodium to be reused in the hydroformylation reaction, the aqueous rhodium-containing extract is fed to a precarbonylation stage where it subjected to a required precarbonylation in the presence of an essentially water-insoluble organic liquid and in the presence of carbon monoxide, synthesis gas or another gas mixture containing carbon monoxide at from 50 to 1000 bar and from 50 to 180° C. The mixture discharged from this precarbonylation stage is then separated into an organic phase containing the main part of the rhodium and an aqueous phase containing the complexing agent. The resulting rhodium-containing organic phase with the regenerated catalyst is then fed into the hydroformylation stage to complete its recycle.

27 Claims, 1 Drawing Sheet

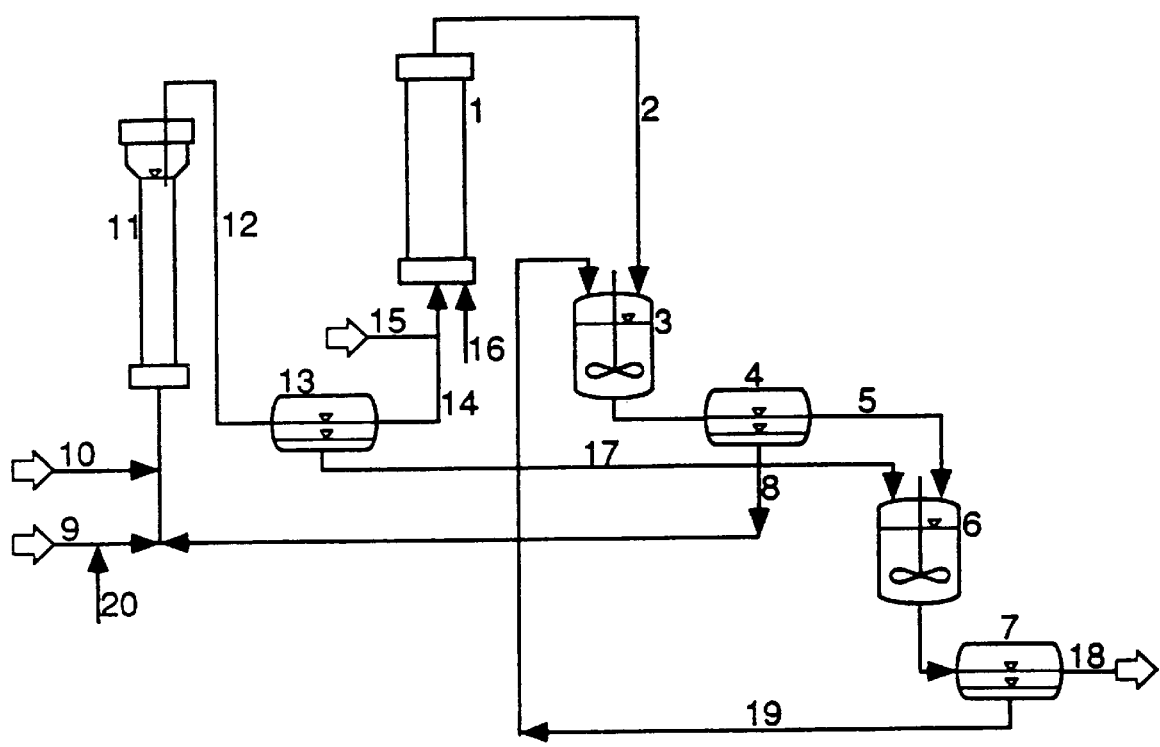

PREPARATION OF ALCOHOLS AND/OR ALDEHYDES

This application is a 371 of PCT/EP95/00825 filed Mar. 6, 1995.

The present invention relates to a process for the preparation of alcohols and/or aldehydes by hydroformylation of olefins of more than 3 carbon atoms, comprising hydroformylation by means of a rhodium catalyst homogeneously dissolved in the reaction medium, the separation of the rhodium catalyst from the mixture discharged from the hydroformylation reaction and the recycling of the rhodium separated from the discharged hydroformylation mixture to the hydroformylation stage.

The hydroformylation of olefins with carbon monoxide and hydrogen in the presence of transition metal catalysts is known. While $\alpha$-olefins can be very readily hydroformylated with rhodium-containing, phosphine-modified catalysts (cf. J. Falbe, Ed: New Syntheses With Carbon Monoxide, Springer, Berlin 1980, page 55 et seq.), this catalyst system is not very suitable for internal and internal, branched olefins and for olefins of more than 7 carbon atoms (cf. Falbe, page 95 et seq.). Thus, internal carbon-carbon double bonds are only very slowly hydroformylated in the presence of such a catalyst. Since the separation of the hydroformylation product from the catalyst dissolved homogeneously in the reaction system is generally effected by distillation and the boiling point of the aldehyde formed in the hydroformylation increases with the increasing number of carbon atoms and chain length to temperatures at which the rhodium-containing catalyst decomposes, this hydroformylation method is not economical for the hydroformylation of olefins of more than 7 carbon atoms. In the hydroformylation of polymeric olefins, for example of polyisobutene, the catalyst containing noble metal cannot be recovered in a reusable form.

On the other hand, internal and internal, branched olefins can advantageously be hydroformylated with uncomplexed rhodium, ie. with rhodium compounds dissolved homogeneously in the hydroformylation medium and not modified with phosphorus-containing ligands, such as phosphines or phosphites. Such rhodium catalysts not modified with phosphines or phosphites and the suitability thereof as catalysts for the hydroformylation of the above-mentioned classes of olefins are known (cf. Falbe, page 38 et seq.). The terms uncomplexed rhodium and uncomplexed rhodium catalysts are used in this application for rhodium hydroformylation catalysts which, in contrast to conventional rhodium hydroformylation catalysts, are not modified with ligands, in particular not with phosphorus-containing ligands, such as phosphine or phosphite ligands, under the conditions of the hydroformylation. Ligands in this context are not understood as including carbonyl or hydrido ligands. In the technical literature (cf. Falbe, page 38 et seq.), it is assumed that the rhodium compound $HRh(CO)_4$ is the catalytically active rhodium species in the hydroformylation with uncomplexed rhodium catalysts, although this has not been unambiguously proven owing to the many chemical mechanisms proceeding side by side in the hydroformylation reaction zone. We make use of this assumption in this application only for the sake of simplicity without as a result restricting the scope of protection of the present application if in the future a rhodium species other than the stated one should prove to be the actual catalytically active species. Under the conditions of the hydroformylation reaction, the uncomplexed rhodium catalysts are formed from rhodium compounds, for example rhodium salts, such as rhodium(III) chloride, rhodium(III) nitrate, rhodium(III) acetate, rhodium (II) acetate, rhodium(III) sulfate or rhodium(III) ammonium chloride, from rhodium chalcogenides, such as rhodium(III) oxide or rhodium(III) sulfide, from salts of rhodium oxo acids, for example the rhodates, from rhodium carbonyl compounds, such as $Rh_4(CO)_{12}$ and $Rh_6(CO)_{16}$, or from organorhodium compounds, such as dicarbonylrhodium acetonylacetonate or cyclooctadienylrhodium acetate or chloride, in the presence of $CO/H_2$ mixtures, which are referred to generally as synthesis gas. For carrying out hydroformylations with uncomplexed rhodium, reference is made at this point, by way of example, to the following publications: U.S. Pat. No. 4,400,547; DE-A 33 38 340; DE-A 26 04 545; WO 82/03856; Chem. Ber. 102 (1969), 2238; Tetrahedron Lett. 29 (1968), 3261; Hydrocarbon Process. (1975), 85–86.

However, the hydroformylation with uncomplexed rhodium also has the disadvantage that, as a result of the thermal stress in the distillative working up of the hydroformylation product, the thermally unstable rhodium catalyst (cf. U.S. Pat. No. 4,400,547) undergoes partial decomposition to metallic rhodium, which is deposited on the walls of the reactor and of the pipes. The precipitated rhodium metal cannot be recycled to the hydroformylation reaction since it cannot be converted into the catalytically active rhodium compound under the hydroformylation conditions. The rhodium losses resulting from this chemical behavior of the uncomplexed rhodium catalysts have to date prevented greater industrial use of this process.

DE-A 33 38 340 and U.S. Pat. No. 4,400,547 describe processes for hydroformylation by means of uncomplexed rhodium catalysts, in which a phosphine or phosphite is added to the discharged hydroformylation mixture to prevent rhodium deposition and, by forming phosphine and/or phosphite complexes, protects the rhodium catalyst from thermal decomposition in the course of the distillative working up of the discharged hydroformylation mixture. After the end of the distillation, the rhodium-containing bottom product of the distillation is treated with an oxidizing agent, the rhodium being liberated in catalytically active form from the relevant phosphine or phosphite complexes, and the phosphine and phosphite ligands being oxidized to the corresponding phosphine oxides and phosphates which do not form rhodium complexes under hydroformylation conditions. The oxidized bottom product of the distillation is then used again as a catalyst for the hydroformylation. The oxidized phosphorus compounds formed in the oxidation do not as a rule present problems in the hydroformylation but, as a result of the process, the oxidized phosphorus compounds accumulate in this hydroformylation circulation, and a bleed stream of this catalyst solution therefore has to be constantly removed from the hydroformylation circulation and replaced by fresh catalyst solution. The catalyst solution removed must be subjected to a special procedure for recovering the rhodium present therein.

WO 82/03856 relates to a process for the thermal stabilization of unmodified, ie. uncomplexed, rhodium catalysts, in which the mixture discharged from the hydroformylation reaction is treated with an oxygen-containing gas, with the result that the aldehydes formed are partially oxidized to the corresponding carboxylic acids, which, together with the rhodium catalyst, form thermally stable rhodium carboxylates in the distillative working up, which carboxylates can be used again as catalysts for the hydroformylation. The disadvantage of this process is the reduction in the yield owing to the partial oxidation of the resulting aldehydes to carboxylic acids. Moreover, this process is limited to hydroformylations in which distillable products are formed: thus, it is not possible in this process, for example, to separate the rhodium catalyst from the hydroformylation product of polyisobutene.

According to U.S. Pat. No. 3,984,478, a hydroformylation process in which the hydroformylation is carried out in the presence of an unsulfonated or sulfonated phthalocyanine was developed in order to avoid rhodium losses. Since some of the rhodium phthalocyanine complexes formed here are sparingly soluble or soluble only in water but not in the organic hydroformylation medium, the hydroformylation is carried out alternatively in the presence of the solid rhodium phthalocyanines or in the two-phase system with water. However, the coordinate bond between the rhodium and the phthalocyanine in these complexes is very strong, so that the rhodium remains bonded to the phthalocyanine even under the hydroformylation conditions. Consequently, the hydroformylation reaction takes place only at the boundary between the hydroformylation medium and solid phthalocyanine or at the boundary with the aqueous rhodium phthalocyanine complex solution, with the result that the reaction rate and thus also the space-time yield of the hydroformylation reaction are so low that this process cannot be economically operated.

There is to date no economically satisfactory process for the direct preparation of internal, ie. branched, aldehydes, ie. isoaldehydes, by hydroformylation of α-aldehydes, ie. aldehydes having a terminal double bond. Bott (Fette, Seifen, Anstrichmittel, 76 (1974), 443) describes the synthesis of internal aldehydes from α-olefins by the isomerization thereof by means of cobalt octacarbonyl ($Co_2(CO)_8$) under a carbon monoxide atmosphere at 190° C. or over a sodium-on-alumina catalyst and the subsequent hydroformylation of the internal olefins by means of homogeneous triphenylphosphinerhodium catalysts. The disadvantage here is the use of two different catalysts for the individual reaction steps. Furthermore, internal olefins react too slowly with the triphenylphosphinerhodium catalyst for industrial purposes.

According to Fell et al. (Tetrahedron Lett., 29 (1968), 3261), oct-1-ene is isomerized to internal olefins at a carbon monoxide pressure of 100 bar and 190° C. over a catalyst which was prepared from $Rh_2O_3$ under 200 bar ($CO/H_2$ (1/1)) cold pressure and at 150° C. in hexane and which had been freed from hydrogen by repeatedly forcing in carbon monoxide. The disadvantage of this process is the expensive preparation of the catalyst, the use of an inert solvent, which occupies a considerable part of the available high-pressure reaction space and therefore reduces the space-time yield, and the use of different reaction gases in the isomerization stage (carbon monoxide) and in the subsequent hydroformylation stage (synthesis gas). Furthermore, the problem of the catalyst stability and regeneration was not solved by Fell et al. This process is thus likewise uneconomical.

Kinetic and mechanistic studies of the isomerization of α-olefins to internal olefins and of the hydroformylation are published in Kogyo Kagaku Zasski, 72 (1969), 671.

It is an object of the present invention to provide a process for the preparation of aldehydes from long-chain and/or branched olefins with the aid of uncomplexed rhodium catalysts, by means of which on the one hand the problems of the deposition of metallic rhodium in the distillative working up of the hydroformylation product and the separation of the rhodium catalyst from undistillable aldehyde products can be satisfactorily solved. For this purpose, it is intended to find a hydroformylation process in which complex ligands form a coordinate bond to the rhodium catalyst in a reversible manner and as a function of the pressure of the carbon monoxide/hydrogen gas mixture, so that said catalyst is stabilized and can be extracted in a working up procedure involving extraction. After recycling to the hydroformylation reaction, the complexes thus formed should undergo decomplexing reversibly under the applied reaction pressure in the presence of the carbon monoxide/hydrogen gas mixture, and the liberated rhodium compound should once again assume the catalytic properties of the uncomplexed rhodium. The aim was in particular to avoid damage to the complex ligands in the course of the hydroformylation reaction, to minimize the losses of rhodium in the course of the extraction and to design the process in such a way that the hydroformylation of internal olefins is economical and can be carried out with high space-time yields.

It is a further object of the invention to provide a process which permits the preparation of isoaldehydes from α-olefins in an economical manner. In particular, it is intended to avoid the prior art disadvantages described above.

We have found that these objects are achieved by a process for the preparation of alcohols and/or aldehydes by the hydroformylation of olefins of more than 3 carbon atoms, comprising hydroformylation by means of a rhodium catalyst homogeneously dissolved in the reaction medium, the separation of the rhodium catalyst from the mixture discharged from the hydroformylation reaction and the recycling of the rhodium separated from the discharged hydroformylation mixture to the hydroformylation stage, wherein the rhodium catalyst is extracted from the discharged hydroformylation mixture by means of an aqueous solution of a nitrogen-containing complexing agent selected from the group consisting of the unsubstituted or substituted pyridines, quinolines, 2,2'-bipyridines, 1,10-phenanthrolines, 2,2'-biquinolines, 2,2',6',2"-terpyridines and porphines which are sulfonated or carry sulfonated substituents, and/or selected from the group consisting of the carboxylated pyridines, of the carboxylated quinolines, and of the unsubstituted or substituted 2,2'-bipyridines, 1,10-phenanthrolines, 2,2'-biquinolines, 2,2',6',2"-terpyridines and porphines which are carboxylated or carry carboxylated substituents, into the aqueous phase, and the alcohol and/or aldehyde are isolated from the extracted discharged hydroformylation mixture, the aqueous rhodium-containing extract is fed to a precarbonylation stage and is subjected to precarbonylation in the precarbonylation stage in the presence of an essentially water-insoluble organic liquid and in the presence of carbon monoxide, synthesis gas or a carbon monoxide-containing gas mixture at from 50 to 1000 bar and from 50 to 180° C., the mixture discharged from the precarbonylation stage is separated into an organic phase containing the main part of the rhodium and into an aqueous phase containing the complexing agent, and the organic phase is fed to the hydroformylation stage for hydroformylation of the olefin at from 50 to 1000 bar and from 50 to 180° C.

According to the invention, the rhodium-containing discharged hydroformylation mixtures obtained in the hydroformylation with uncomplexed rhodium are mixed with water-soluble, nitrogen-containing complexing agents, preferably polydentate complexing agents, which, together with the rhodium catalyst, form complexes which are hydrophilic and, owing to their good water solubility, can be extracted with water from the organic medium of the discharged hydroformylation mixture. After the rhodium catalyst contained in the discharged hydroformylation mixture has been separated off by extraction in the form of a water-soluble complex with the complexing agent used according to the invention, the hydroformylation product can be worked up in a conventional manner, for example by isolating said product by distillation from the organic extract or by distilling off more readily volatile organic components of the discharged hydroformylation mixture from the more sparingly volatile or possibly even undistillable hydroformylation product. The aqueous extract of the discharged hydroformylation mixture, which contains the rhodium catalyst now complexed by the nitrogen-containing complexing agent, is fed to a processing stage in which the complexed rhodium catalyst is carbonylated in the presence of an essentially water-insoluble, organic liquid and in the presence of carbon monoxide, synthesis gas or a carbon monoxide-containing gas mixture at in general from 50 to 1000, preferably from 70 to 500, particularly preferably from 100 to 400, bar and at from 50 to 180° C., preferably from 70 to 160° C., in particular from 90 to 140° C. As a result of the carbonylation, the rhodium is removed from the hydrophilic complex with the nitrogen-containing complexing agent, and the resulting lipophilic rhodium carbonyl compound migrates as uncomplexed rhodium into the water-insoluble, organic liquid. This step is referred to as precarbonylation since the carbonylation of the rhodium takes place not in the hydroformylation reactor itself but in effect in the precarbonylation stage upstream of said reactor.

The mixture discharged from the precarbonylation stage can be readily separated, for example in a phase separator, into an organic phase containing the main part of the rhodium in the form of a rhodium carbonyl compound and into an aqueous phase containing the main part of the complexing agent. The organic phase is then fed to the hydroformylation stage, in which the uncomplexed rhodium contained in this catalyst solution catalyzes the hydroformylation of the olefin to be hydroformylated. The aqueous phase containing the main part of the complexing agent can be used in another manner, for example advantageously for extracting the rhodium catalyst from the discharged hydroformylation mixture.

The use of such a precarbonylation stage has considerable advantages. Since the carbonylation is generally carried out more rapidly and under milder conditions than the hydroformylation reaction, on the one hand the nitrogen-containing complexing agent can be exposed to less stringent reaction conditions during a shorter residence time and protected in this manner, and on the other hand the same space-time yield can be obtained using smaller reactor dimensions, since the aqueous phase no longer enters the hydroformylation reactor.

The precarbonylation can be carried out with the aid of carbon monoxide, synthesis gas or a carbon monoxide-containing gas mixture. Synthesis gas is understood as meaning $CO/H_2$ gas mixtures in which carbon monoxide and hydrogen are generally present in a molar ratio of from 1:5 to 5:1, preferably from 4:6 to 6:4. For the purposes of this application, carbon monoxide-containing gas mixtures are understood as meaning other carbon monoxide-containing gas mixtures which are not covered by the term synthesis gas, for example $CO/H_2$ mixtures having a composition differing from that of the synthesis gas, or mixtures of carbon monoxide with other gases which are inert under the reaction conditions, such as nitrogen, noble gases or lower hydrocarbons, such as methane, ethane, propane or butane.

According to the invention, a large number of liquids which are inert under the reaction conditions of the precarbonylation stage and of the hydroformylation stage can be used as essentially water-insoluble organic liquid, the term inert meaning that these liquids do not adversely affect the course of the precarbonylation or of the hydroformylation.

Organic liquids of this type which may be used are, for example, hydrocarbons. However, aldehydes or alcohols or mixtures of aldehydes and alcohols are preferably used. For example, some of the crude mixture discharged from the hydroformylation stage can be used for this purpose, but it is also possible to use the aldehydes or alcohols formed in the hydroformylation stage and subsequently isolated, or mixtures thereof. There is virtually no limit with regard to the type of aldehydes used as water-insoluble, organic liquid in the precarbonylation stage. However, aldehydes or alcohols as formed in the hydroformylation of the olefin to be hydroformylated are preferably used.

High boilers may also be used as essentially water-insoluble, organic liquid in the precarbonylation stage. These are high-boiling condensation products of aldehydes, which are formed as by-products in the course of the hydroformylation. They are of course generally multi-component mixtures. U.S. Pat. No. 4,148,830 describes, by way of example, the chemical nature of such mixtures of high boilers. Said mixtures are also commercially available, for example under the name Texanol® from Eastman.

In the novel process, olefins are particularly preferably used as essentially water-insoluble, organic liquid in the precarbonylation stage. Although there is in principle no limit with regard to the type of olefin used in the precarbonylation, olefins such as those used in the subsequent hydroformylation stage are preferably employed.

It may also prove advantageous to pass the total olefin feed for the hydroformylation stage initially through the precarbonylation stage. If synthesis gas is used as the carbonylating agent in the precarbonylation stage, the olefin introduced may be hydroformylated in small amounts in the precarbonylation itself, depending on the chosen conditions. If carbon monoxide or carbon monoxide-containing gas mixtures are used as the carbonylating agent, acyl complexes of carbonylated rhodium may form with the olefin, with the result that additional stabilization of the homogeneously dissolved rhodium can be achieved.

It has been found, surprisingly, that isomerization of the α-olefins to internal olefins may take place when α-olefins are used in the precarbonylation stage. According to the invention, α-olefins can therefore be isomerized to internal olefins and the latter hydroformylated in the downstream hydroformylation stage to give internal, ie. branched, aldehydes. This is particularly advantageous since α-olefins are available on the market in larger amounts than internal olefins, α-olefins are also more economically obtainable than internal olefins, and branched aldehydes and branched alcohols are desirable intermediates for the preparation of branched carboxylic acids, alcohols and amines, which in turn are used extensively, for example as additives for detergents and cleaning agents and for the preparation of biodegradable surfactants.

For the preparation of branched alcohols and/or aldehydes from α-olefins by the novel process, the α-olefin feed is advantageously passed through the precarbonylation stage. The precarbonylation and, simultaneously, the isomerization of the α-olefin to the internal olefin are generally carried out at from 100 to 180° C., preferably from 120 to 160° C., particularly preferably from 130 to 150° C., and at from 50 to 1000, preferably from 70 to 500, particularly preferably from 100 to 400, bar. The residence time required for complete isomerization of the α-olefin in the precarbonylation stage is in general dependent on the reaction conditions used therein and is advantageously determined by a preliminary experiment.

In the novel process, it is of course also possible to hydroformylate α-olefins to n-aldehydes, for example by introducing the α-olefin into the hydroformylation reactor with bypassing of the precarbonylation stage, or by choosing the reaction conditions in the precarbonylation stage so that the α-olefin fed to the precarbonylation stage is not significantly isomerized.

The precarbonylation stage may consist of one reactor or a plurality of reactors connected in parallel or in series. Conventional stirred autoclaves may be used for this purpose in a batchwise procedure, and stirred autoclave cascades or tube reactors which contain apparatuses suitable for thorough mixing of the reaction mixture may be used in a continuous procedure.

The mixture discharged from the precarbonylation stage is separated in a suitable apparatus, for example a phase separator, into an aqueous and an organic phase. The phase separation can be carried out under superatmospheric pressure, for example under the operating pressure of the precarbonylation stage, or at atmospheric pressure, after prior letting down of the mixture discharged from the precarbonylation. Since both the precarbonylation and the hydroformylation are carried out under superatmospheric pressure, the phase separation is advantageously also carried out under superatmospheric pressure.

The organic phase which is separated off from the mixture discharged from the precarbonylation stage, and which contains the uncomplexed rhodium required for catalysis of the hydroformylation and, depending on the type of water-insoluble, organic liquid used in the precarbonylation stage, the olefin to be hydroformylated or another suitable organic liquid, can be fed to the hydroformylation stage. If the discharged precarbonylation mixture was not let down and degassed, the organic phase still contains the gaseous carbonylating agent used in the precarbonylation stage, said agent being essentially in dissolved form.

The hydroformylation with the aid of the uncomplexed rhodium catalyst produced in the precarbonylation stage is carried out in the presence of synthesis gas. If necessary, the olefin to be hydroformylated is also fed to the hydroformylation stage, unless it has already been fed to the hydroformylation stage with the organic phase from the discharged precarbonylation mixture.

The hydroformylation is generally carried out at from 60 to 180° C., preferably from 80 to 140° C., particularly preferably from 90 to 130 ° C., and at in general from 50 to 1000, preferably from 70 to 500, in particular from 100 to 400, bar. The hydroformylation is carried out otherwise under conditions as usually used in hydroformylations with uncomplexed rhodium and as described, for example, in the literature cited at the outset, relating to hydroformylation with uncomplexed rhodium.

The product ratio alcohol/aldehyde in the discharged hydroformylation mixture may be influenced, depending on the pressure and temperature conditions used in the hydroformylation stage and on the synthesis gas composition. For example, in the hydroformylation of trimeric propylene with the same synthesis gas compositions ($CO/H_2$ molar ratio 50/50, 40/60 and 60/40) at 130° C. and 280 bar, an aldehyde/alcohol molar ratio of 93/7 is obtained in each case. When the temperature is increased from 130° C. to 150° C., the aldehyde/alcohol molar ratio in the discharged hydroformylation mixture changes to 76/24, 67/33 and 82/18, respectively, depending on the synthesis gas composition ($CO/H_2$ molar ratio 50/50, 40/60 and 60/40, respectively).

The hydroformylation can be carried out in the presence or absence of organic solvents. The use of organic solvents is particularly advantageous, especially in the hydroformylation of long-chain or polymeric olefins. The solvents usually employed in the hydroformylation process can be used as solvents, for example high-boiling aromatic and aliphatic hydrocarbons or high-boiling aldehyde condensation products which are formed as by-products in the course of the hydroformylation reaction as a result of the condensation of the aldehydes obtained as products.

The mixture discharged from the hydroformylation stage is advantageously let down before being extracted with the aqueous solution of the nitrogen-containing complexing agent. The extraction of the discharged hydroformylation mixture is generally carried out at from 80 to 140° C., preferably from 90 to 130° C., in particular from 100 to 120° C., and at in general from 1 to 20, preferably from 1 to 10, particularly preferably from 1 to 5, bar. The extraction can be carried out in the air or under an inert gas atmosphere, for example a nitrogen, hydrogen or argon atmosphere, but it may also be advantageous additionally to mix carbon monoxide or synthesis gas with the inert gas used or to carry out the extraction in the presence of carbon monoxide.

For the extraction of the rhodium catalyst from the discharged hydroformylation mixture, it is possible to use a fresh aqueous solution of the complexing agent, but the aqueous phase obtained in the phase separation of the discharged precarbonylation mixture and containing the dissolved complexing agent is preferably used for this, said aqueous phase being recycled to the extraction stage for this purpose.

A volume ratio of aqueous to organic phase of in general 0.2–2, preferably 0.3–1, is as a rule established in the extraction. The molar ratio of nitrogen-containing complexing agent to rhodium in the extraction is in general from 5:1 to 10,000:1, preferably from 10:1 to 5000:1, in particular from 50:1 to 1000:1.

Virtually all liquid-liquid extraction apparatuses are suitable for extracting the discharged hydroformylation mixture with the aqueous solution of the complexing agent, for example mixer-settler apparatuses, bubble columns or countercurrent or cocurrent extraction columns, which may also be provided with additional baffles for better mixing of the aqueous and organic phases, for example with sieve trays, packings or static mixers. The extraction of the rhodium catalyst from the discharged hydroformylation mixture can be carried out in a single stage, but a multistage extraction is preferably employed, for example a two-stage or three-stage extraction, and the aqueous phase containing the complexing agent can be fed cocurrent with, or particularly preferably countercurrent to, the organic phase.

After the end of the extraction, the discharged hydroformylation mixture freed from the rhodium catalyst can be worked up in a conventional manner, for example by distillation, in order to isolate the desired products contained therein, i.e. alcohols and/or aldehydes.

BRIEF DESCRIPTION OF THE DRAWINGS

An advantageous embodiment of the novel process is shown schematically in the FIGURE and is described below. Self-evident details of the plant which are not required for illustrating the novel process were not included in the FIGURE, for the sake of clarity. The embodiment of the novel process shown in the FIGURE comprises the process stages of hydroformylation, a two-stage countercurrent extraction of the discharged hydroformylation mixture by means of mixer-settler apparatuses and the precarbonylation stage. Of course, other extraction apparatuses from among those stated above may also be used instead of the mixer-settler apparatuses.

In the embodiment of the novel process according to the FIGURE, the discharged hydroformylation mixture from the hydroformylation reactor 1 is let down and, if necessary, mixed with inert gas (not shown) and then introduced via pipe 2 into the extraction stage A comprising the mixer-settler apparatus 3/4 and is extracted there with the aqueous solution of the nitrogen-containing complexing agent from extraction stage C (mixer-settler apparatus 6/7), fed in via pipe 19. When the plant is started up, or for replenishment of the solution of complexing agent, fresh solution of complexing agent can be fed, for example, to the mixer 3, via an inlet not shown in the FIGURE. The extraction mixture contained in the mixer 3 is separated in the settler 4 into a first organic and a first aqueous phase. The first aqueous phase is passed via pipe 8 into the precarbonylation reactor, whereas the first organic phase is fed via pipe 5 to the extraction stage C. Before being passed into the precarbonylation reactor 11, the first aqueous phase is mixed, in suitable mixing apparatuses, via the feeds 9 and 10, with an essentially water-insoluble, organic liquid, for example crude discharged hydroformylation mixture, Texanol® or, preferably, the olefin to be hydroformylated, and with the carbonylating agent, ie. carbon monoxide, synthesis gas or a suitable carbon monoxide-containing gas mixture, preferably with carbon monoxide or synthesis gas. It is in principle also possible for the starting materials fed in via the pipes 9 and 10 to be introduced directly into the precarbonylation reactor 11. In the precarbonylation reactor 11, the rhodium bonded to the nitrogen-containing complexing agent and present in the aqueous phase is carbonylated under the stated conditions, and the resulting lipophilic uncomplexed rhodium catalyst migrates into the organic phase. The mixture discharged from the precarbonylation reactor 11 is passed via pipe 12, preferably without being let down beforehand, into the phase separator 13, where it is separated into a second organic and a second aqueous phase (phase separation B).

The second organic phase, which, in addition to the water-insoluble, organic liquid, also contains, in dissolved form, the uncomplexed rhodium required for catalyzing the hydroformylation and, if required, excess carbonylating agent, is passed via pipe 14 into the hydroformylation reactor 1. Synthesis gas is passed via pipe 15 into the hydroformylation reactor but may alternatively be passed directly into hydroformylation reactor 1. If an olefin was not used as the water-insoluble, organic liquid in the precarbonylation reactor, the olefin to be hydroformylated may be either introduced directly via pipe 16 into the hydroformylation reactor 1 or mixed beforehand, via an inlet not shown in the FIGURE, with the stream in pipe 14. In the hydroformylation reactor, the olefin is hydroformylated under the stated conditions to give the corresponding alcohols and/or aldehydes.

The second aqueous phase from phase separation B, which contains the rhodium-poor solution of the nitrogen-containing complexing agent, is let down and then fed to the mixer 6 via pipe 17. In extraction stage C, comprising the mixer 6 and the settler 7, the first organic phase from extraction stage A is extracted again with the second aqueous phase from phase separation B, in order to remove residual amounts of rhodium from the first organic phase. The extraction mixture contained in the mixer 6 is separated in the settler 7 into a third organic and a third aqueous phase. The third organic phase now freed from rhodium is discharged via pipe 18 for further working up to isolate the desired products alcohol and/or aldehyde. The third aqueous phase from extraction C is passed via pipe 19 into the extraction stage A, thus closing the circulation.

The first filling of the reactor with rhodium can be effected by introducing a solution or suspension of the rhodium catalyst or one of the precursor compounds stated at the outset and suitable for the preparation of the rhodium catalyst, for example into the precarbonylation reactor 11 or into the hydroformylation reactor 1. The same applies to any necessary replenishment of spent catalyst. It is also possible to introduce the rhodium into the plant via pipe 20 or other inlets not shown in the FIGURE, for example via an inlet in pipe 8.

Sulfonated, nitrogen-containing complexing agents, such as sulfonated pyridines or sulfonated quinolines, and/or water-soluble carboxylated pyridines or quinolines, are preferably used as complexing agents which form water-soluble complexes with the rhodium catalyst dissolved in the mixture discharged from the hydroformylation reaction. Polydentate, in particular bidentate, tridentate or tetradentate, sulfonated nitrogen-containing complexing agents are preferably used, 2,2'-bipyridine sulfonates, 2,2'-biquinoline sulfonates, 1,10-phenanthroline sulfonates, 2,2', 6',2"-terpyridine sulfonates or porphine sulfonates being particularly preferred. The use of polydentate, in particular bidentate, tridentate or tetradentate, carboxylated, nitrogen-containing complexing agents in the novel process is also particularly preferred, especially the use of 2,2'-bipyridine carboxylates, 1,10-phenanthroline carboxylates, 2,2'-biquinoline carboxylates, 2,2',6',2"-terpyridine carboxylates and porphine carboxylates.

Under the action of these complexing agents, coordinate bonds to the central rhodium atom of the rhodium catalyst are formed, presumably via the free electron pair of the nitrogen atoms, some of the carbon monoxide bonded to the central rhodium atom of the rhodium catalyst presumably being reversibly displaced by these ligands under the conditions of complex formation. The presence of sulfonate or carboxylate groups in the nitrogen-containing complexing agents used according to the invention is critical for the feasibility of the novel process. The complexing agents may contain one or more carboxylate and/or sulfonate groups per molecule, the number of carboxylate and/or sulfonate groups in the molecule being of course also dependent on the size of the molecule of the complexing agent and its reactivity with respect to sulfonating reagents. For example, as a rule monosulfonated pyridines and 2,2'-bipyridines are used as complexing agents, whereas the sulfonated porphines may contain, for example, up to 4 sulfonate groups in the molecule. Since carboxylate-carrying nitrogen-containing complexing agents can advantageously be prepared by oxidizing the corresponding alkyl-substituted, preferably methyl-substituted, complexing agents, which are readily obtainable by conventional chemical processes, the carboxylated complexing agents may carry from 1 to 6, preferably from 1 to 4, and particularly preferably from 1 to 3, carboxyl groups, depending on the size of the molecule. The number of carboxyl and/or sulfo groups in the molecule of the complexing agent influences the water solubility of these complexing agents. In the novel process, it is of course also possible to use nitrogen-containing complexing agents which contain both carboxyl groups and sulfo groups as substituents or to use mixtures of sulfonated and carboxyl-containing complexing agents. In the complexing agents used according to the invention, the sulfonate and carboxylate groups are preferably present in salt form, in particular in the form of water-soluble salts, particularly preferably in the form of their onium, alkali metal and/or alkaline earth metal salts. The type of onium salt used is in general not critical. For example, ammonium, phosphonium or arsonium salts of the relevant carboxylic or sulfonic acids may be employed. To avoid misunderstandings, it is expressly pointed out here that the nitrogen-containing complexing agent sulfonates or carboxylates which can be used according to the invention carry the sulfonate or carboxylate groups as substituents and are not bonded to any sulfonate or carboxylate anions, for example in the form of a salt.

The stated complexing agents may additionally be substituted by substituents which are inert under the reaction conditions, such as halogen, in particular fluorine, chlorine or bromine, alkyl, in particular $C_1$–$C_4$-alkyl, aryl, in particular $C_6$–$C_{10}$-aryl, $C_7$–$C_{12}$-aralkyl, nitro, hydroxyl, cyano, alkoxy, in particular $C_1$–$C_4$-alkoxy, and $C_1$–$C_{10}$-alkylsulfonate groups.

Substitution by alkyl, aryl or aralkyl may be advantageous particularly when the nitrogen-containing complexing agent has low reactivity and can be sulfonated only under drastic conditions. Since carbocyclic aryl and aralkyl groups are often easier to sulfonate than electron-deficient, nitrogen-containing heterocycles, such as pyridine or bipyridine, in the case of such a substitution of the heterocycle, or in the case of fusion of aromatic, nonheterocyclic ring systems with the nitrogen-containing heterocycle, sulfonation can be carried out under substantially milder conditions without these nitrogen-containing complexing agents substituted in this manner being adversely affected by such a substitution in their property as complexing agents for the novel process. The same also applies to the case of alkyl substitution of the nitrogen-containing complexing agent, since the aliphatic side chains can in general by readily converted, for example by means of sulfuryl chloride, into the corresponding sulfochlorides, the basic hydrolysis of which gives the corresponding sulfonates.

The sulfonated nitrogen-containing complexing agents can be produced from the corresponding, unsulfonated parent compounds by conventional sulfonation processes, such as the reaction with concentrated sulfuric acid or oleum, in the presence or absence of catalysts, such as mercury sulfate, or by the reaction of these compounds with halosulfonic acids, preferably with chlorosulfonic acid, and subsequent hydrolysis of the resulting sulfonyl halides to give the sulfonic acid salts. Alkanesulfonate-substituted complexing agents, such as pyridine-4-ethanesulfonate, are obtainable, for example, by sulfochlorination of the corresponding parent compounds, in the case stated above by way of example, 4-ethylpyridine, by means of sulfuryl chloride and subsequent alkaline hydrolysis of the resulting sulfochloride.

This and other methods which can be used for the preparation of sulfonated complexing agents are described in C. Ferri, Reaktionen der organischen Synthese, pages 165–172 and 484–485, Thieme, Stuttgart 1978. For example, 2,2'-bipyridine-5-sulfonic acid is obtainable by sulfonating 2,2'-bipyridine by the process described by Herrmann et al., Chem. Ber. 123 (1990), 1953. 1,10-Phenanthroline can be sulfonated in a similar manner. Further sulfo-substituted bipyridines can be prepared according to Campa et al., An. Quim., Ser. C 84 (1988), 128. The terpyridines, which can be prepared, for example, by the methods stated by Kröhnke in Synthesis 1 (1976), can likewise be converted into the relevant sulfonates by the processes stated by Ferri.

The sulfonation of the nitrogen-containing complexing agents by the methods stated above generally gives isomer mixtures of the sulfonated complexing agents, which carry the sulfonate groups in the various possible positions of the nitrogen-containing ring system of the complexing agent and/or in the substituents bonded to the ring system of the complexing agent, in particular in the aromatic substituents, such as phenyl or naphthyl. Polysulfonation of these complexing agents frequently occurs, particularly in the case of the more complicated ring systems of the complexing agents and in the case of the complexing agents having aromatic substituents. The complexing agent sulfonate mixtures obtained by the various sulfonation methods and consisting of isomeric, monosulfonated complexing agents and polysulfonated complexing agents can of course be separated into the individual sulfonated components by the prior art methods, such as crystallization or ion exchange chromatography, and the individual components thus obtained can be used as complexing agents in the novel process. Since, however, the site of the sulfonation and the degree of sulfonation of the sulfonated complexing agents are generally not critical for the result of the novel process and the success of the novel process is generally dependent only on the fact that the nitrogen-containing complexing agents are sulfonated, the mixtures of the complexing agent sulfonates obtained by the various sulfonation methods are preferably used in the novel process, advantageously after they have been converted into their water-soluble salts, with the result that separation into the sulfonated individual components of the complexing agent sulfonate mixture is unnecessary. For this reason, as a rule no reference is made to the individual sulfonates of the various complexing agents for the purpose of this application; instead, the relevant complexing agents are referred to by group, for example as quinoline sulfonates, 2,2'-biquinoline sulfonates, 1,10-phenanthroline sulfonates, terpyridine sulfonates, etc. Individual, sulfonated complexing agents are mentioned by name in this application only in exceptional cases, if the relevant sulfonated complexing agent is virtually exclusively formed, under the reaction conditions usually used, in certain sulfonation processes for the sulfonation of specific complexing agents.

To illustrate the large number of complexing agents which may be used according to the invention, a number of nitrogen-containing complexing agents which can be used in the novel process after sulfonation according to the above-mentioned methods and conversion into their salts are stated below by way of example: pyridine, the picolines, other alkylpyridines, quinoline, 5,6-benzoquinoline, 2,2'-bipyridine, 2,2'-biquinoline of the formula I

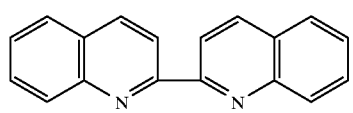

I 5,6,5',6'-dibenzo-2,2'-biquinoline of the formula II

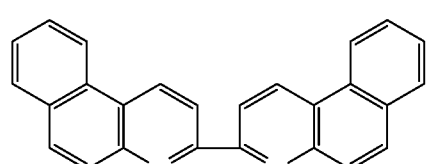

II 1,10-phenanthroline, 2,9-dimethylphenanthroline, 4,7-diphenyl-1,10-phenanthroline (bathophenanthroline) of the formula III

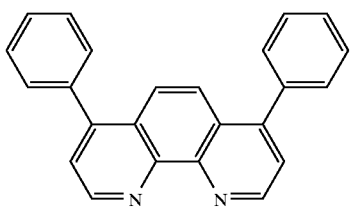

2,9-dimethyl-4,7-diphenyl-1,10-phenanthroline (bathocuproin) of the formula IV

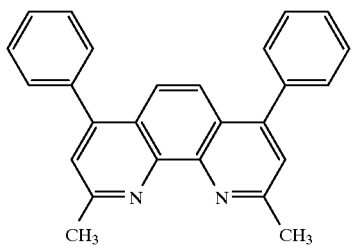

4,5-diazafluorene V

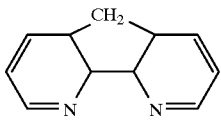

dipyrido[3,2-a: 2',3'-c]phenazine of the formula VI (compounds V and VI are obtainable according to Aust. J. Chem. 23 (1970), 1023)

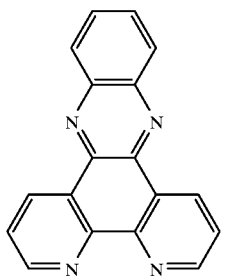

2,2',6',2"-terpyridine of the formula VII

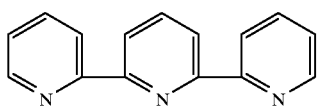

4'-phenyl-2,2',6',2"-terpyridine of the formula VIII

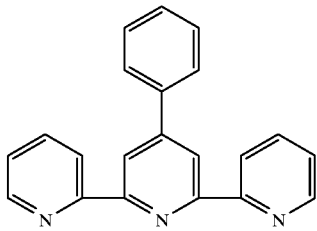

4-methyl-4'-phenyl-4"-methyl-2,2',6',2"-terpyridine of the formula IX

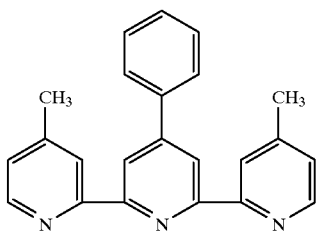

and the porphines.

The sulfonated nitrogen-containing complexing agents whose properties as complexing agents may be attributed to the structural element, contained in the respective complexing agents, of the 2,2'-bipyridine, 1,10-phenanthroline and 2,2',6',2"-terpyridine ring system have proven particularly suitable for the novel process, as is the case, for example, for the above-mentioned compounds of the formulae I to IX.

The carboxyl-carrying complexing agents can be prepared from the compounds I to IX which are monosubstituted to hexasubstituted, preferably monosubstituted to tetrasubstituted, particularly preferably monosubstituted to trisubstituted, by methyl, by oxidation of the methyl groups, for example by means of potassium permanganate. The methyl-substituted or benzofused compounds I to IX can be obtained, for example, by the processes as described by Kröhnke et al., Synthesis 1 (1976); Sasse et al., J. Chem. Soc. 616 (1956); Sasse et al., J. Heterocycl. Chem. 8 (1971), 483; Bos et al., Synth. Commun. 9 (1979), 497, or Elliot et al., J. Am. Chem. Soc. 104 (1982), 7519. The oxidation of the methyl groups to carboxyl groups can be carried out, for example, with potassium permanganate by the methods which can be generally used, as described by Anderson et al. (J. Chem. Soc. Dalton Trans. 2247 (1985)) or Hanabusa et al. (Makromol. Chem. 190 (1989), 1). Among the carboxyl-carrying, nitrogen-containing complexing agents, the use of 2,2'-bipyridine-4,4'-dicarboxylic acid and of 2,2'-bipyridine-5,5'-dicarboxylic acid or of the salts thereof is preferred.

The novel process is particularly suitable for the hydroformylation of olefins with more than 3, preferably more than 7, carbon atoms, in particular for the hydroformylation of $C_7$–$C_{20}$-olefins which may be straight-chain or branched and may contain α-olefinic and/or internal double bonds, eg. oct-1-ene, dodec-1-ene, trimeric and tetrameric propylene or dimeric, trimeric and tetrameric butylene. Unsaturated oligomers of other olefins can also be hydroformylated, as can cooligomers of different olefins. The aldehydes formed from these olefins are used, for example, as intermediates for the preparation of plasticizer alcohols and surfactants, which can be produced therefrom in a conventional manner by hydrogenation. The olefins used for the hydroformylation can be obtained, for example, by acid-catalyzed elimination of water from the corresponding fatty alcohols or by a large number of other industrial processes, as described, for example, in Weissermel, Arpe: Industrielle Organische Chemie, pages 67–86, Verlag Chemie, Weinheim, 1978. If α-olefins are used in the novel process, they can be alternatively hydroformylated to the corresponding n-aldehydes by direct introduction into the hydroformylation stage or hydroformylated to isoaldehydes, the use of which has already been referred to, by introduction of said olefins into the precarbonylation stage after they have been isomerized to internal olefins.

The novel process is also particularly suitable for the hydroformylation of polymeric olefins, for example low molecular weight polyisobutene, low molecular weight polybutadiene or low molecular weight 1,3-butadiene/isobutene or butene copolymers. Low molecular weight polymers are understood as meaning in particular polymers having molecular weights of from 500 to 5000 Dalton. However, relatively high molecular weight, unsaturated polymers may also be hydroformylated. The only precondition for this is that they are soluble in the hydroformylation medium. The hydroformylation products of these polymeric olefins, in particular those of low molecular weight polyisobutene, can be converted by reductive amination, for example by the process of EP-A 244 616, into the corresponding amines, which are used as fuel additives. Low molecular weight polyisobutene is obtainable, for example, by the process of EP-A 145 235, and low molecular weight isobutene/1,3-butadiene copolymers can be obtained, for example, by the process of German Patent Application P 4306384.5.

The novel process is suitable in practice for the preparation of all aldehydes which are obtainable by the hydroformylation of olefins. In particular, it is pointed out that, for example, substituted olefins which in general may carry 1 or 2 substituents, preferably one substituent, can also be hydroformylated by the novel process. For example, unsaturated, aliphatic carboxylates, acetals, alcohols, ethers, aldehydes, ketones, amines and amides can be hydroformylated by the novel process. Substituted starting olefins of this type which are of interest are, for example, methacrylates, dicyclopentadiene, vinyl and allyl ethers, in particular appropriately substituted derivatives of unsaturated fatty acids, for example the esters of oleic, linoleic, linolenic, ricinoleic or erucic acid. The aldehydes obtainable from these olefinic raw materials by hydroformylation are likewise starting materials for the preparation of readily biodegradable, washing-active substances.

A further embodiment of the present invention relates to processes for the preparation of branched carboxylic acids, alcohols or amines from α-olefins, the α-olefins being isomerized to internal olefins by the novel process in the precarbonylation stage and then hydroformylated to isoaldehydes, and the isoaldehydes thus obtained being oxidized to branched carboxylic acids, reduced to branched alcohols or subjected to reductive amination to give branched amines in a conventional manner.

The oxidation of the isoaldehydes or isoaldehyde/n-aldehyde mixtures obtained according to the invention from α-olefins can be carried out in a conventional manner, for example by oxidation of the aldehydes with atmospheric oxygen or oxygen by the processes as described, for example, in Ullmann's Encyclopedia of Industrial Chemistry, Vol. A5, page 239, VCH Verlagsgesellschaft, Weinheim, 1986.

The catalytic hydrogenation of the isoaldehydes or isoaldehyde/n-aldehyde mixtures obtainable from α-olefins by the novel process to give branched alcohols can be carried out in a manner known per se, for example by the processes described in Ullmann's Encyclopedia of Industrial Chemistry, 5th Edition, Vol. A1, page 279, VCH Verlagsgesellschaft, Weinheim, 1985, or G. H. Ludwig, Hydrocarbon Processing, March 1993, page 67.

The reductive amination of the isoaldehydes or isoaldehyde/n-aldehyde mixtures obtainable from α-olefins by the novel process can be carried out in a manner known per se, for example by the processes described in Ullmann's Encyclopedia of Industrial Chemistry, 5th Edition, Vol. A2, page 1, VCH Verlagsgesellschaft, Weinheim, 1985. Ammonia, primary C1-C20-amines or secondary C2-C20-amines may be used as starting materials for the preparation of amines.

EXAMPLES

In the Examples which follow, the word bipyridine represents the sodium salt of 2,2'-bipyridine-5-sulfonic acid.

Example 1

Precarbonylation in the presence of crude oxo product of trimeric propylene 50 g of a 2.8% strength by weight aqueous bipyridine solution, which was enriched with about 100 ppm by weight of rhodium by extraction of the crude mixture discharged from the hydroformylation of trimeric propylene, were stirred vigorously together with 50 ml of crude, rhodium-free oxo product of trimeric propylene in a pressure-resistant reactor at 130° C. and 280 bar $CO/H_2$ (molar ratio 1:1) for 1 hour. After cooling, the mixture discharged from this carbonylation was let down, and the resulting two-phase mixture was analyzed to determine its rhodium content. The organic phase contained 55 ppm by weight of rhodium, and the aqueous phase 6 ppm by weight thereof.

Example 2

Precarbonylation in the presence of aldehyde 24 ml of a 2.8% strength by weight aqueous bipyridine solution, which was enriched with about 100 ppm by weight of rhodium after extraction of crude oxo product of trimeric propylene, was stirred vigorously together with 30 ml of isodecanol in a pressure-resistant reactor at 130° C. and 280 bar $CO/H_2$ (molar ratio 1:1) for 1 hour. After cooling to room temperature, the mixture discharged from the precarbonylation was let down, and the resulting two-phase mixture was analyzed to determine its rhodium content. The organic phase contained 70 ppm by weight of rhodium, and the aqueous phase 10 ppm by weight thereof.

Example 3

Precarbonylation in the presence of alcohol 24 ml of a 2.8% strength by weight aqueous bipyridine solution, which was enriched with about 100 ppm by weight of rhodium after extraction of crude oxo product of trimeric propylene, was stirred vigorously together with 24 g of isodecanol in a pressure-resistant reactor at 130° C. and 280 bar $CO/H_2$ (molar ratio 1:1) for 1 hour. After cooling to room temperature and letting down the pressure, the resulting two-phase precarbonylation mixture was analyzed to determine its rhodium content. The organic phase contained 50 ppm by weight of rhodium, and the aqueous phase 38 ppm by weight thereof.

Example 4

Precarbonylation with carbon monoxide in the presence of olefin 50 g of the 2.8% strength by weight bipyridine solution used in the above Examples were stirred vigorously together with 100 g of trimeric propylene in a pressure-resistant reactor at 130° C. and 280 bar CO for 1 hour. After cooling to room temperature and letting down the pressure, the organic phase of the discharged precarbonylation mixture contained 60 ppm by weight of rhodium, and the aqueous phase 19 ppm by weight thereof.

Example 5
Precarbonylation and subsequent hydroformylation 60 g of trimeric propylene and 30 ml of the bipyridine solution used in the above Examples were stirred vigorously in an autoclave at 130° C. and 280 bar CO/H$_2$ (molar ratio 1:1) for 1 hour. The organic phase of the discharged precarbonylation mixture contained 36 ppm by weight of rhodium, and the aqueous phase 80 ppm by weight thereof. A further 81 g of trimeric propylene were added to 19 g of the organic phase, and hydroformylation was carried out in the autoclave at 130° C. and 280 bar CO/H$_2$ (molar ratio 1:1) for 3 hours. 112.5 g of product having an aldehyde content of 76% by weight and an alcohol content of 3.9% by weight were obtained. 18% of the trimeric propylene had not reacted.

Example 6
Precarbonylation/isomerization and hydroformylation of an α-olefin 68 ml of dodec-1-ene and 25 ml of the bipyridine solution used in the above Examples were stirred vigorously in an autoclave at 130° C. and 280 bar CO for 1 hour. The organic phase of the discharged precarbonylation mixture contained 29 ppm by weight of rhodium, and the aqueous phase 16 ppm by weight thereof. 32.7 g of the organic phase were hydroformylated in an autoclave at 90° C. and 280 bar CO/H$_2$ (molar ratio 1:1) for 3 hours. According to gas chromatographic analysis, the discharged hydroformylation product contained 98.2% by weight of tridecanals in addition to 1.2% by weight of unconverted dodecenes (isomer mixture). The amount of n-tridecanal was only 16% by weight. The amount of methyldodecanal was 24.9% by weight, and a further 57.4% by weight consisted of a mixture of different internal tridecanals.

Example 7
Extraction of a discharged hydroformylation mixture at 85° C. under atmospheric pressure 42 g of an aqueous bipyridine solution in which the rhodium content had been reduced according to Examples 1 and 2 (rhodium content: 9.2 ppm by weight) were added to 90 g of oxo product from the hydroformylation of trimeric propylene, having a rhodium content of 74 ppm by weight, at 85° C. under a nitrogen atmosphere at atmospheric pressure, and the mixture was stirred for 30 minutes. After phase separation, the organic phase still contained 17 ppm by weight of rhodium, and the aqueous phase 83 ppm by weight thereof.

Example 8
Multistage extraction of a discharged hydroformylation mixture at 120° C. under superatmospheric pressure 100 g of the oxo product from the hydroformylation of trimeric propylene, having a rhodium content of 67 ppm by weight, were extracted twice while stirring in the course of 30 minutes at 120° C. under a nitrogen atmosphere at 3 bar with 50 g of a bipyridine solution which was obtained according to Examples 1 and 2 and in which the rhodium content had been reduced (rhodium content: 7.4 ppm by weight). After the pressure had been let down and the phases separated, the organic phase contained less than 0.5 ppm by weight of rhodium. The rhodium content of the aqueous bipyridine solution was 127 ppm by weight after the first extraction and 21 ppm by weight after the second extraction.

Example 9
Multistage extraction of a discharged hydroformylation mixture under a hydrogen atmosphere 112 g of the oxo product from the hydroformylation of trimeric propylene, having a rhodium content of 55 ppm by weight, were extracted twice while stirring (30 minutes) under a hydrogen atmosphere at 120° C. and 4.2 bar with a 2.8% strength by weight aqueous bipyridine solution (rhodium content: 9.2 ppm by weight), this being carried out similarly to Example 7. After this procedure, the organic phase contained 1.1 ppm by weight of rhodium, the aqueous phase from the first extraction contained 140 ppm by weight of rhodium and the second aqueous phase from the second extraction contained 16 ppm by weight of rhodium.

We claim:

1. In a process for the preparation of an aldehyde, an alcohol or mixtures thereof by the hydroformylation of an olefin of more than 3 carbon atoms in a hydroformylation stage at a pressure of from 50 to 1000 bar and a temperature of from 50 to 180° C. by means of a hydrogen/carbon monoxide gas mixture in the presence of an uncomplexed rhodium catalyst homogeneously dissolved in the reaction medium, extracting the rhodium catalyst from the mixture discharged from the hydroformylation stage of the reaction and into an aqueous phase by means of an aqueous solution of a nitrogen-containing complexing agent selected from the group consisting of sulfonated pyridines, sulfonated quinolines, the unsubstituted or substituted 2,2-bipyridines, 1,10-phenanthrolines, 2,2'-biquinolines, 2,2', 6', 2''-terpyridines, and porphines which are sulfonated or carry sulfonated substituents, and further from the group consisting of the carboxylated, the carboxylated quinolines, the unsubstituted or substituted 2,2'-bipyridines, 1,10-phenanthrolines, 2,2'-biquinolines, 2,2', 6', 2''-terpyridines and porphines which are carboxylated or carry carboxylated substituents, thereafter isolating said aldehyde, alcohol or their mixed product from the resulting extracted and discharged reaction mixture and recycling the extracted rhodium catalyst to the hydroformylation stage, the improvement which comprises:

feeding the aqueous rhodium-containing extract to a separate precarbonylation stage where it is subjected to carbonylation in the presence of an essentially water-insoluble organic liquid and also in the presence of carbon monoxide, the hydrogen/carbon monoxide synthesis gas mixture or another carbon monoxide-containing mixture at from 50 to 1000 bar and from 50 to 180° C., separating the mixture discharged from the precarbonylation stage into an organic phase containing the main part of the rhodium and an aqueous phase containing the complexing agent, and then feeding the organic phase containing the uncomplexed rhodium catalyst into said hydroformylation stage.

2. A process as claimed in claim 1, wherein the extraction of the rhodium catalyst from the discharged hydroformylation mixture is carried out at from 80 to 140° C. and from 1 to 20 bar.

3. A process as claimed in claim 1, wherein the extraction of the rhodium catalyst is carried out in one or more stages, and the aqueous solution of the complexing agent is fed countercurrent to the discharged hydroformylation mixture in the extraction.

4. A process as claimed in claim 1, wherein the aqueous phase containing the complexing agent is recovered from the precarbonylation stage by separating off the organic phase containing the main part of the rhodium, and the recovered aqueous phase is then used for extracting the rhodium catalyst from the discharged hydroformylation mixture.

5. A process as claimed in claim 1, wherein the process is carried out continuously in a plant comprising a precarbonylation unit, a hydroformylation unit and a one-stage or multistage extraction unit.

6. A process as claimed in claim 1, wherein the olefins used are straight-chain or branched α-olefins, which are unsubstituted or substituted by 1 or 2 substituents which are inert under the reaction conditions, or internal olefins or mixtures of these olefins, in the presence or absence of a solvent.

7. A process as claimed in 1, wherein propene or butene oligomers or cooligomers are hydroformylated.

8. A process as claimed in claim 1, wherein low molecular weight polyisobutenes, polybutadienes or isobutene/1,3-butadiene copolymers are hydroformylated.

9. A process as claimed in claim 1, wherein unsaturated fatty acid derivatives are hydroformylated.

10. A process as claimed in claim 1 for the reaction of said olefin of more than 3 carbon atoms with a synthesis gas in a hydroformylation stage followed by at least two extraction stages to purify and recover the reaction product, wherein:
   the mixture discharged from the hydroformylation stage is extracted in a first extraction stage A with an aqueous solution of the nitrogen-containing complexing agent as withdrawn from a second extraction stage C, and said mixture extracted from stage A is separated into a first aqueous phase and a first organic phase with said first aqueous phase being fed to the precarbonylation stage and said first organic phase being fed to the second extraction stage C;
   in the precarbonylation stage, the rhodium contained in said first aqueous phase is carbonylated with carbon monoxide, synthesis gas or a carbon monoxide-containing gas mixture in the presence of an essentially water-insoluble, organic liquid;
   the mixture discharged from the precarbonylation stage is separated in a phase separation step B into a second organic phase and a second aqueous phase with the second organic phase being fed to the hydroformylation reaction and the second aqueous phase being fed to said extraction stage C;
   using the second aqueous phase from step B for extracting residual rhodium catalyst from the first organic phase in extraction stage C;
   separating the extraction mixture from extraction stage C into a third organic phase and a third aqueous phase;
   isolating the aldehyde, alcohol or their mixtures product from the third organic phase, and recycling the third aqueous phase to the extraction stage A for extracting the rhodium catalyst from the discharged hydroformylation mixture.

11. A process as claimed in claim 1, wherein the crude mixture discharged from the hydroformylation stage is used in the precarbonylation stage as the essentially water-insoluble organic liquid.

12. A process as claimed in claim 1, wherein an aldehyde or alcohol is used in the precarbonylation stage as the essentially water-insoluble organic liquid.

13. A process as claimed in claim 12, wherein the aldehyde or alcohol or their mixture formed in the hydroformylation stage is purified and is then used in said precarbonylation stage.

14. A process as claimed in claim 1, wherein a mixture of high-boiling condensation products of aldehydes is used in the precarbonylation stage as the essentially water-insoluble organic liquid.

15. A process as claimed in claim 1, wherein an olefin is used in the precarbonylation stage as the essentially water-insoluble organic liquid.

16. A process as claimed in claim 15, wherein the olefin used in said precarbonylation stage is the olefin to be hydroformylated in said hydroformylation stage.

17. A process as claimed in claim 15, wherein an internal olefin is used.

18. A process as claimed in claim 15, wherein an α-olefin is used.

19. A process as claimed in claim 15, wherein the precarbonylation is carried out at from 100 to 180° C. and from 50 to 1000 bar.

20. A process as claimed in claim 15, wherein the precarbonylation is carried out in the presence of carbon monoxide.

21. A process as claimed in claim 15, wherein the precarbonylation is carried out in the presence of the synthesis gas.

22. A process as claimed in claim 1, wherein the nitrogen-containing complexing agent used is a water-soluble salt of 2,2'-bipyridine-5-sulfonic acid.

23. A process as claimed in claim 1, wherein the nitrogen-containing complexing agent used is the water-soluble salt of a sulfonated 1,10-phenanthroline.

24. A process as claimed in claim 1, wherein the nitrogen-containing complexing agent used is a water-soluble salt of 2,2'-bipyridine-4,4'-dicarboxylic acid or of 2,2'-bipyridine-5,5'-dicarboxylic acid.

25. A process for the preparation of a carboxylic acid from an internal olefin or an α-olefin, wherein the olefin is hydroformylated as claimed in claim 1, and the aldehyde formed is subsequently oxidized to the carboxylic acid.

26. A process for the preparation of an alcohol from an internal olefin or an α-olefin, wherein the olefin is hydroformylated as claimed in claim 1, and the aldehyde formed is subsequently reduced or hydrogenated to the alcohol.

27. A process for the preparation of an amine from an internal olefin or an α-olefin, wherein the olefin is hydroformylated as claimed in claim 1, and the aldehyde or alcohol formed is aminated with ammonia or a primary or secondary amine in the presence of an amination catalyst and hydrogen.

* * * * *